US011850372B1

(12) United States Patent
Mokarram-Dorri et al.

(10) Patent No.: US 11,850,372 B1
(45) Date of Patent: Dec. 26, 2023

(54) BI-DIRECTIONAL ACCESS TO TUMORS

(71) Applicant: Duke University, Durham, NC (US)

(72) Inventors: Nassir Mokarram-Dorri, Durham, NC (US); Ravi Bellamkonda, Durham, NC (US); Barun Brahma, Atlanta, GA (US); James Leo Pokorney, Northfield, MN (US); Jack Cabell Griffis, III, Vero Beach, FL (US); Donald Kenneth Griffin, II, Marietta, GA (US)

(73) Assignee: DUKE UNIVERSITY, Durham, NC (US)

(*) Notice: Subject to any disclaimer, the term of this patent is extended or adjusted under 35 U.S.C. 154(b) by 673 days.

(21) Appl. No.: 16/701,448

(22) Filed: Dec. 3, 2019

Related U.S. Application Data

(63) Continuation of application No. 16/432,475, filed on Jun. 5, 2019, now Pat. No. 10,493,233.

(60) Provisional application No. 62/680,893, filed on Jun. 5, 2018.

(51) Int. Cl.
A61M 25/00 (2006.01)
B82Y 15/00 (2011.01)
B82Y 5/00 (2011.01)
A61M 25/02 (2006.01)

(52) U.S. Cl.
CPC .......... *A61M 25/0021* (2013.01); *B82Y 5/00* (2013.01); *B82Y 15/00* (2013.01); *A61L 2400/12* (2013.01); *A61M 2025/006* (2013.01); *A61M 2025/0042* (2013.01); *A61M 2025/0213* (2013.01); *A61M 2210/0687* (2013.01)

(58) Field of Classification Search
CPC ............ A61L 2400/12; A61M 27/006; A61M 25/007; A61M 27/00; A61M 39/0208
See application file for complete search history.

(56) References Cited

U.S. PATENT DOCUMENTS

| 4,159,720 | A | * | 7/1979 | Burton | A61M 5/141 606/232 |
| 4,250,882 | A | * | 2/1981 | Adair | A61M 1/90 604/355 |
| 4,885,002 | A | * | 12/1989 | Watanabe | A61B 5/031 604/9 |
| 4,929,236 | A | * | 5/1990 | Sampson | A61M 39/12 604/905 |
| 5,846,220 | A | * | 12/1998 | Elsberry | A61M 25/0068 128/898 |
| 6,852,106 | B2 | * | 2/2005 | Watson | A61M 39/0208 604/288.03 |

(Continued)

FOREIGN PATENT DOCUMENTS

| WO | WO-9614834 A1 | * | 5/1996 | ........... A61K 9/0024 |
| WO | WO-2012047931 A1 | * | 4/2012 | ........... A61K 9/0024 |
| WO | WO-2020132529 A1 | * | 6/2020 | ........... A61M 25/02 |

*Primary Examiner* — William R Carpenter
(74) *Attorney, Agent, or Firm* — Talem IP Law, LLP

(57) ABSTRACT

An apparatus for guiding the migration of cancer and other cells includes a reservoir device, a cover, a tube, a nanofiber structure, and a lock device. The reservoir device defines a reservoir having an open top. The cover is configured for removable installation over the open top of the reservoir. The tube has a proximal end portion reaching into the reservoir. The nanofiber structure communicates an inlet port in the tube with the reservoir. The lock device interlocks the tube with the reservoir device, and also interlocks the nanofiber structure with the reservoir device.

22 Claims, 13 Drawing Sheets

(56) References Cited

U.S. PATENT DOCUMENTS

| | | | |
|---|---|---|---|
| 10,493,233 B1* | 12/2019 | Mokarram-Dorri | ......................... A61M 25/0021 |
| 2008/0114308 A1* | 5/2008 | di Palma | ............... A61M 39/10 604/533 |
| 2012/0065625 A1* | 3/2012 | Nelson | .................. A61M 39/12 604/533 |
| 2013/0172846 A1* | 7/2013 | Bellamkonda | ....... A61K 47/593 604/500 |
| 2018/0071501 A1* | 3/2018 | Volkodav | ............ A61M 27/006 |
| 2018/0140810 A1* | 5/2018 | Cataltepe | .......... A61M 25/0097 |

\* cited by examiner

BI-DIRECTIONAL ACCESS TO TUMORS

RELATED APPLICATIONS

This application claims priority of provisional U.S. Patent Application 62/680,893, filed Jun. 5, 2018, which is incorporated herein by reference.

TECHNICAL FIELD

This technology includes implantable devices for the treatment of tumors.

BACKGROUND

Tumor cells are known to migrate as described in U.S. patent application Ser. No. 13/814,009, published as U.S. Patent Publication 2013/0172846. As described in that application, an implantable apparatus directs tumor cells to migrate away from a tumor for elimination at a remote location that is more readily accessible to a surgeon. The apparatus includes two surgically implantable scaffolds that are separate from one another. The first scaffold includes a nanofiber film with first and second end portions, and is free of a cytotoxic agent. The second scaffold is configured for surgical implantation and resection separately from the first scaffold. The second scaffold can thus be deployed adjacent the second end portion of the nanofiber film at an implanted location remote from the tumor. A cytotoxic agent is provided for contacting and killing the migrated tumor cells received at the second scaffold.

SUMMARY

An apparatus for guiding the migration of cells and/or other bioactive entities may include a tube, a reservoir device, and a nanofiber structure. The reservoir device defines a reservoir. The nanofiber structure reaches outward from the tube and into the reservoir.

In an embodiment presented as an example, the tube has a lumen, a side wall, an outlet opening, and an inlet opening. The inlet opening reaches through the side wall at a location spaced longitudinally from the outlet opening. The nanofiber structure reaches within the lumen past the inlet opening, and reaches outward from the lumen through the outlet opening.

The inlet opening can be one of multiple inlet openings that are spaced apart around the side wall of the tube. The nanofiber structure can be one of multiple nanofiber structures, each of which reaches within the lumen past a respective inlet opening and outward from the lumen through the outlet opening.

In an illustrated embodiment, a lock device interlocks the nanofiber structure with the tube. The lock device may also interlock the tube with the reservoir device. The reservoir may have an open top, and the apparatus may further include a cover configured for removable installation over the open top of the reservoir.

DETAILED DESCRIPTION

Figure 2:
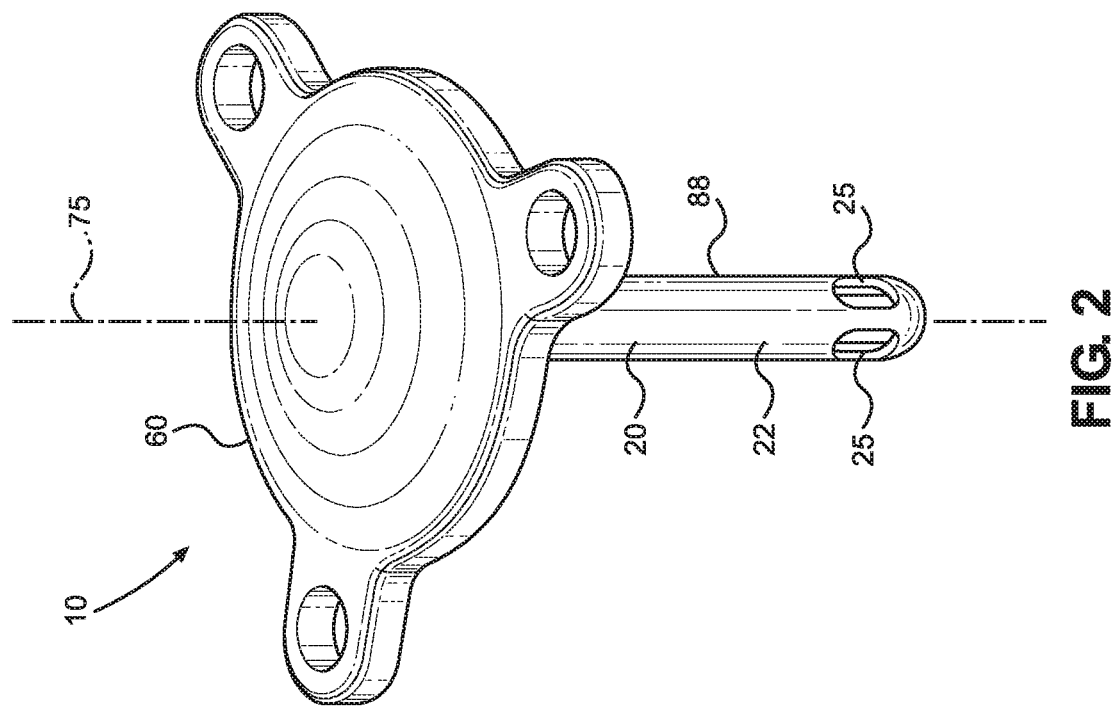
FIG. 2 is a perspective view of the apparatus of FIG. 1.

The embodiments illustrated in the drawings include examples of the structural elements recited in the claims. The illustrated embodiments thus include examples of how a person of ordinary skill in the art can make and use the claimed invention. They are described here to provide enablement and best mode without imposing limitations that are not recited in the claims. One or more elements of one embodiment may be used in combination with, or as a substitute for, one or more elements of another as needed for any particular implementation.

The illustrated embodiments are described in the context of guiding the migration of cancer cells in a direction away from a tumor. However, the claimed apparatus can provide bi-directional access to a tumor for excavating or transplanting cells, sampling and/or delivering small molecules, chemicals, drugs, adjuvants, cells, mRNA, proteins, or other biologics and non-biologics (herein termed "bioactive entities"). These bioactive entities may be endogenously derived or exogenously derived. The claimed apparatus thus provides bi-directional as well as more facile access to tumors. Such an apparatus can be used alone or in conjunction with other treatments of tumors including immune-therapy, chemotherapy, and/or radiation therapy.

More specifically, access to tumors can be critical to delivery therapy, monitoring status, and customizing therapy. The illustrated embodiments of the apparatus include a component with a port and another component with a reservoir. The first component is implantable with the port close to a tumor. The second component is connected to the first at a location that is readily accessible to a physician or nurse practitioner. The apparatus has the ability to move cancer cells from the tumor to an accessible point, or to move other cells and/or other bioactive entities (exogenous or endogenous) from the reservoir to the tumor site. In addition, due to the two components being connected, the apparatus allows for equilibrating the content of the apparatus to the environment of either the open port near the tumor or the remote component, allowing bi-directional sampling of biological matter or chemical matter such as RNA, DNA, cell debris, proteins, drugs, small molecules, or biologics.

Figure 1:
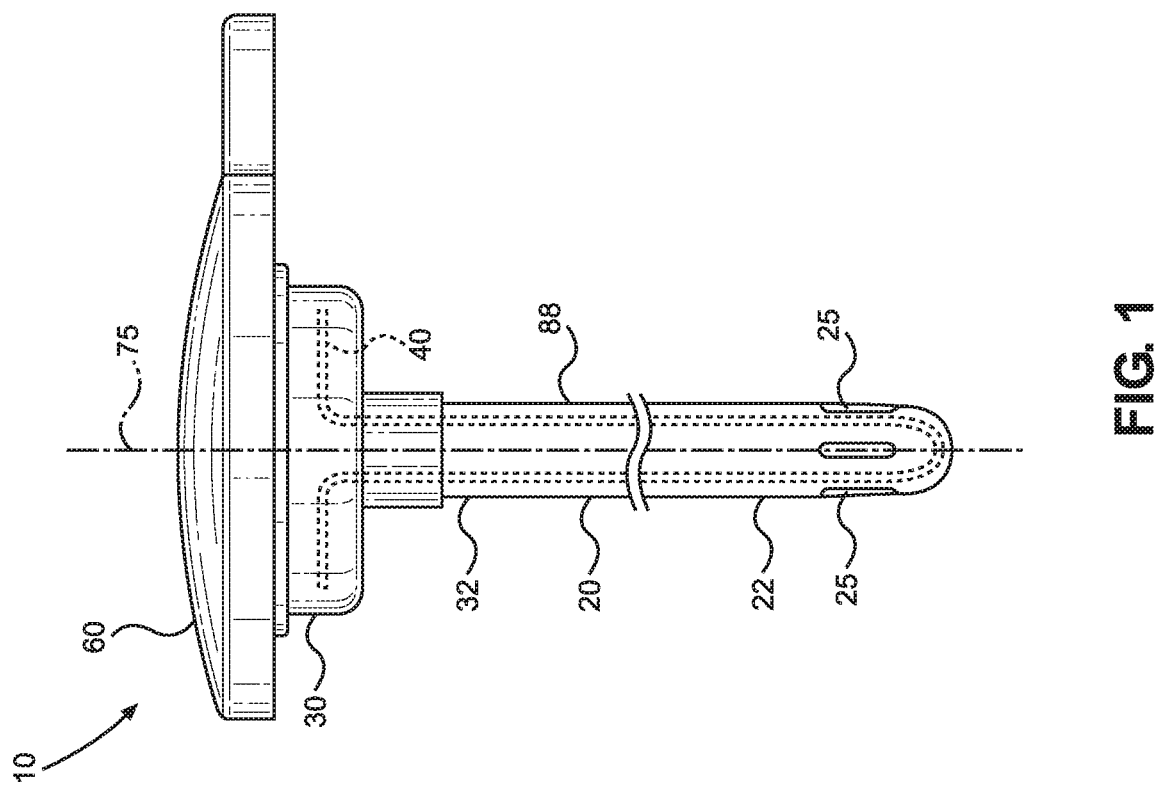
FIG. 1 is a side view of an apparatus for guiding cells.
Figure 3:
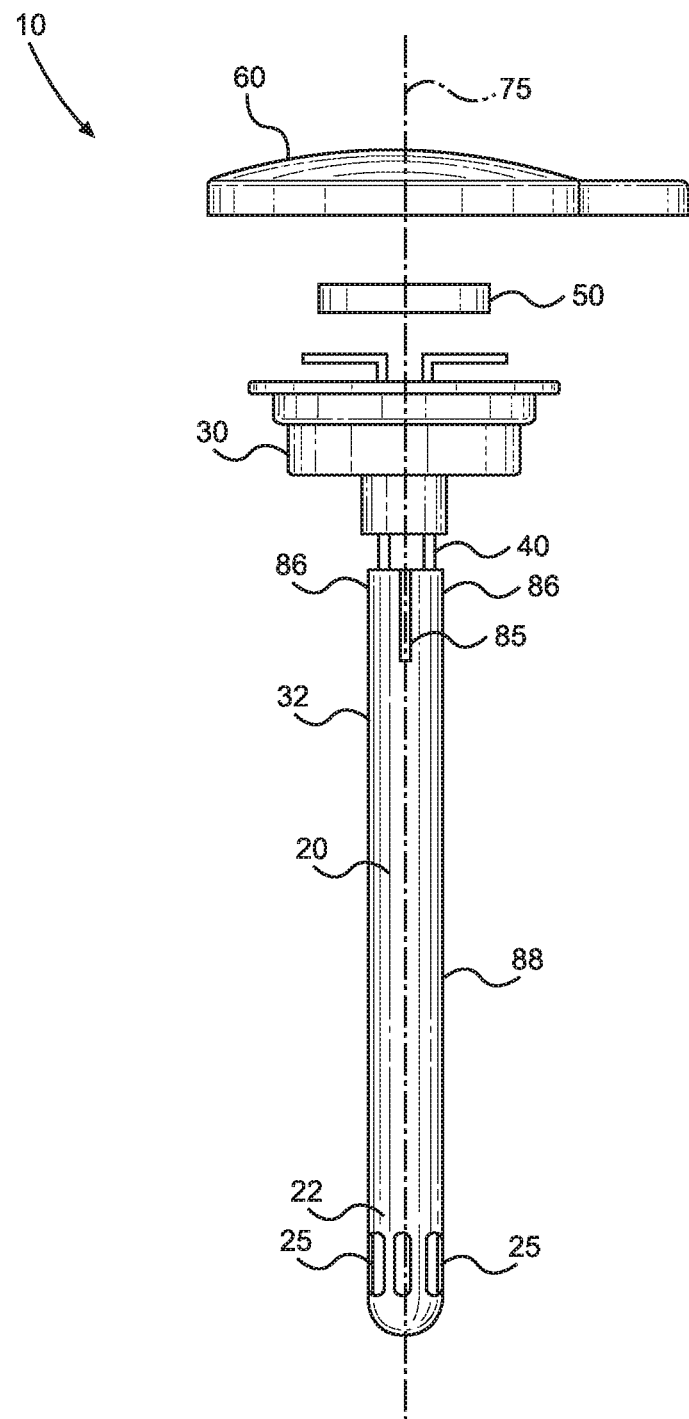
FIG. 3 is an exploded view showing parts of the apparatus of FIG. 1.

An embodiment of an apparatus 10 for guiding the migration of cells and/or other bioactive entities is shown in FIGS. 1 and 2. The apparatus 10 includes a catheter 20 with a distal end portion 22 having inlet openings 25. A reservoir device 30 is mounted on a proximal end portion 32 of the catheter 20. A nanofiber structure 40 reaches within the catheter 20 from the distal end portion 22 to the proximal end portion 32. The nanofiber structure 40 reaches further outward from the proximal end portion 32 of the catheter 20 and into the reservoir device 30. In some embodiments a lock ring 50 (FIG. 3) interlocks the catheter 20 and the nanofiber structure 40 with the reservoir device 30. A cover 60 is removably installed over the reservoir device 30.

This particular embodiment of the apparatus 10 is configured for bi-directionally guiding brain tumor cells and/or other bioactive entities. In use, the reservoir device 30 is implanted within a cranial aperture. The cover 60 is fastened directly to the skull. The catheter 20 reaches within the brain, with the distal end portion 22 penetrating or adjoining a brain tumor. Intra-tumor pressure can then move tumor cells through the inlet openings 25 and into contact with the nanofiber structure 40 at the distal end portion 32 of the catheter 20. The tumor cells can then migrate along the nanofiber structure 40 to the proximal end portion 32 of the catheter 20, and further from the catheter 20 into the reservoir device 30.

The apparatus 10 can also be used to guide other cells or other bioactive entities away from a treatment site. For example, the apparatus can be used for accessing non-brain tumors, and/or for accessing non-tumor cells within the brain or other parts of the body. Alternatively, other bioactive entities may be provided in the reservoir 131, thereby allowing the pother bioactive entities to migrate along the nanofiber structure 40 to the distal end portion 22 of the catheter 20 and out of the inlet openings 25 for delivery to the tumor or other treatment site.

Figure 4:
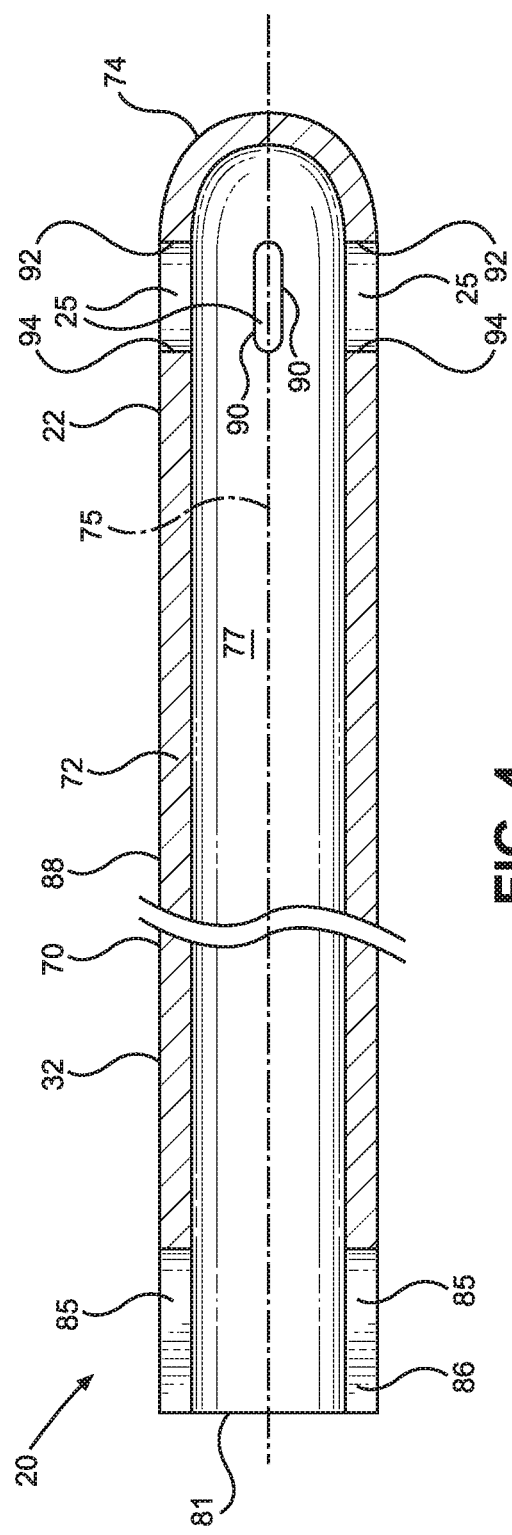
FIG. 4 is a sectional side view of a part of the apparatus of FIG. 1.

As shown separately in FIG. 4, the catheter 20 in the given example consists of a tube with an elongated side wall 72 and an end wall 74. The tube 70 is formed of material that is impervious to cancer cells, and is preferably formed of a flexible material such as a silicone polyurethane co-polymer. The side wall 72 and the end wall 74 can have circular cross-sectional shapes centered on a longitudinal axis 75, and together define a lumen 77, although in other embodiments the side and end walls 72 and 74 can assume other shapes, for example elliptical, regular polygonal, irregular polygonal, etc.. An open proximal end of the side wall 72 defines an outlet opening 81 for the lumen 77. The end wall 74 has a hemispherical contour, and defines a closed distal end of the lumen 77. The inlet openings 25 reach transversely through the side wall 72 to communicate the lumen 77 with the exterior of the catheter 20 adjacent to the end wall 74. A pair of slits 85 define a pair of diametrically opposed proximal sections 86 of the side wall 72 extending distally from the outlet opening 81. The proximal and distal end portions 32 and 22 of the tube 70 are proportionately minor length portions of the tube 70. A major length portion 88 of the tube 70 reaches longitudinally between the proximal and distal end portions 32 and 22, and is free of openings.

The side wall 72 in this embodiment has four inlet openings 25. The inlet openings 25 are located axially adjacent to each other, and are arranged in two diametrically opposed pairs. Each opposed pair of inlet openings 25 is circumferentially offset from the other opposed pair by degrees about the axis 75. One opposed pair of inlet openings 25 is aligned axially with the opposed proximal sections 86 of the side wall 72 at the outlet opening 81. In some embodiments, the number of inlet openings can vary, for example a single inlet opening, two inlet openings, three, five, six, or more inlet openings. The openings can be similarly sized and shaped, or the size, shape, and configuration of the inlet openings can vary.

Figure 5:
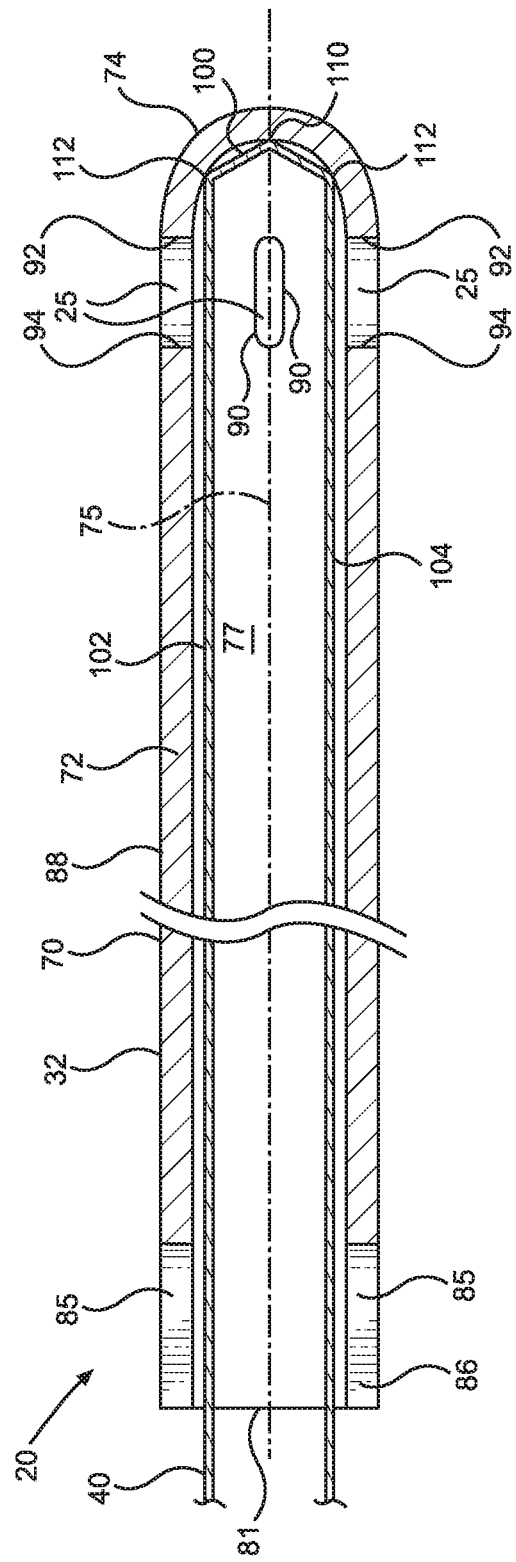
FIG. 5 is a view similar to FIG. 4, showing an additional part of the apparatus.

The nanofiber structure 40 in this embodiment example is configured as a strip of film. As shown in FIG. 5, the film strip 40 is folded into a U-shape with a base 100 and first and second legs 102 and 104. The base 100 is attached to the tube 70 at a central attachment location 110 on the end wall 74. This can be accomplished by, for example, a thermal weld.

The legs 102 and 104 are also attached to the tube 70 at attachment locations 112 on the end wall 74. The attachment locations 112 for the legs 102 and 104 are aligned axially with a diametrically opposed pair of the inlet openings 25, and also with the proximal sections 86 of the side wall 72. Each leg 102 and 104 is unattached to the tube 70 between the respective attachment location 112 and the outlet opening 81. Additionally, the attachment locations 112 for the legs 102 and 104 are spaced transversely inward from the surrounding side wall 72 at locations radially between the axis 75 and the side wall 72. In this arrangement, each leg 102 and 104 of the nanofiber film 40 reaches within the lumen 77 axially from an attachment location 112 toward and past an inlet opening 25 in a position spaced transversely from the inlet opening 25 and the adjacent surfaces of the side wall 72. Such spacing helps to ensure that the adjacent surfaces of the side wall 72 do not contact film 40 so as to block cell migration along the surface of the film 40. Each leg 102 and 104 reaches further to the outlet opening 81, and outward from the lumen 77 through the outlet opening 81.

The strip of nanofiber film 40 is composed of biocompatible polymer nanofibers. The nanofibers are generally aligned coaxially along the length of the film strip 40, and are thus aligned generally coaxially with the lumen 77 when the film strip 40 is in the installed position of FIG. 5. The aligned nanofiber surface of the film 40 structurally mimics the white matter tracks and blood vessels that physically guide the migration of glioma or other cancer cells. This directs migration of the cells along the film 40 from the inlet openings 25 toward and through the outlet opening 81.

Preferably, the average nanofiber diameter is about 650+/−300 nm, and the film thickness is within a range of about 10 to about 300 micrometers. It is also preferred that at least about 50% of the nanofibers, and preferably at least about 80%, have orientations that are aligned within about 20 degrees of the longitudinal direction in which cell migration is guided, which in this example is lengthwise of the film strip 40. This preferred alignment of the nanofibers is most preferably continuous along the length of the film strip 40 to provide directional continuity for cell migration to be guided fully from the inlet openings 25 to the outlet opening 81 along the surface of the film strip 40.

In other embodiments, the nanofiber structure can assume other forms, for example one or more elongated strips that are not curved into a U-shape, a film twisted into a spiral or helical shape, a mesh or web of interconnected nanofiber structures, a tubular film, or any other suitable configuration, as shown and described below with respect to FIGS. 20-23. Other suitable migration-directing structures and materials also can be used, either in addition to a nano-fiber structure or in place of a nanofiber structure. Examples could include differently structured strips of biocompatible material with topographic features and/or chemical attractants that promote and direct migration of cells or other biological material along the strips. Such topographic features could include micro-textured and/or nano-textured grooves that preferably reach lengthwise of the strip with orientations that are aligned within about 20 degrees of a centerline of the strip fully between the catheter inlet openings and the reservoir.

Further regarding the inlet openings 25 in the tube 70, each inlet opening 25 in the illustrated embodiment is shaped as an axially elongated slot with parallel opposite side edges 90 (FIG. 4) reaching between rounded opposite end edges 92 and 94. The slot shape is beneficial regarding both occlusion within the opening 25 and access for the passage of cells through the opening 25. When the tube 70 is being implanted longitudinally, the openings 25 are advanced distally toward the tumor or other target site. Each opening 25 then has a leading edge 92 and a trailing edge 94. The trailing edges 94 can scrape against healthy tissue to cause occlusion of the openings 25. Compared with the slot-shaped opening 25, a circular opening with the same area would have larger trailing edge. The longitudinal elongation of the slot shaped opening 25 thus provides a relatively enlarged open area without enlarging the trailing edge 94. The inlet openings at the distal end portion 22 of the tube 70, in combination with the major length portion 88 that is free of openings, are thus configured as features that enable migration of cells through the tube while simultaneously shielding the surrounding healthy tissue.

Figure 6:
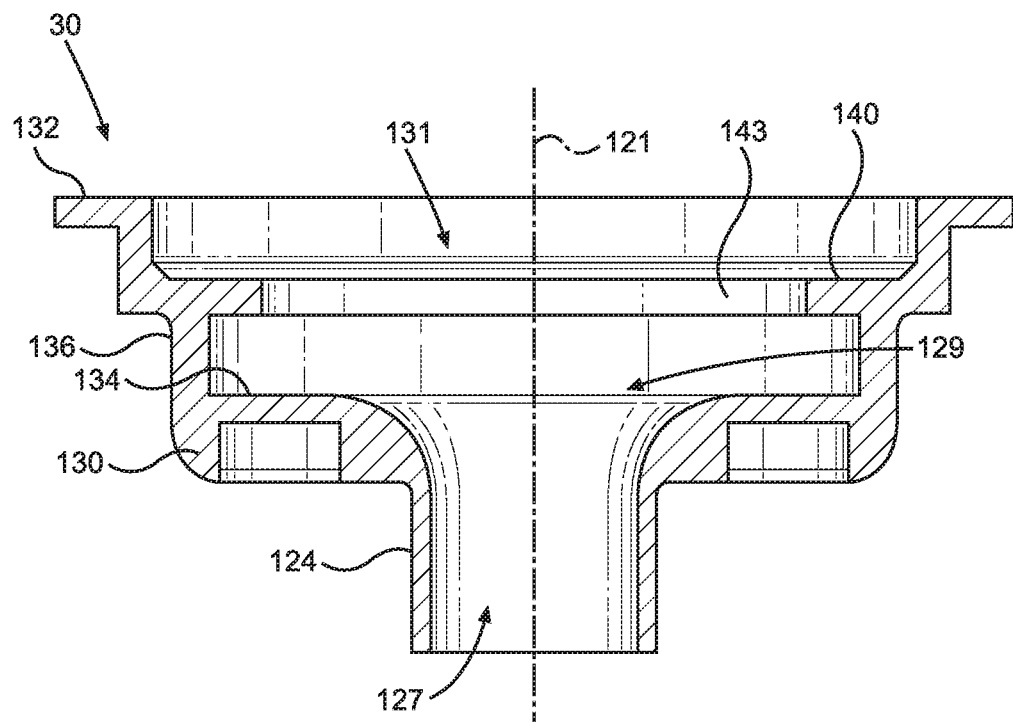
FIG. 6 is a perspective view of a part of the apparatus of FIG. 1.
Figure 7:
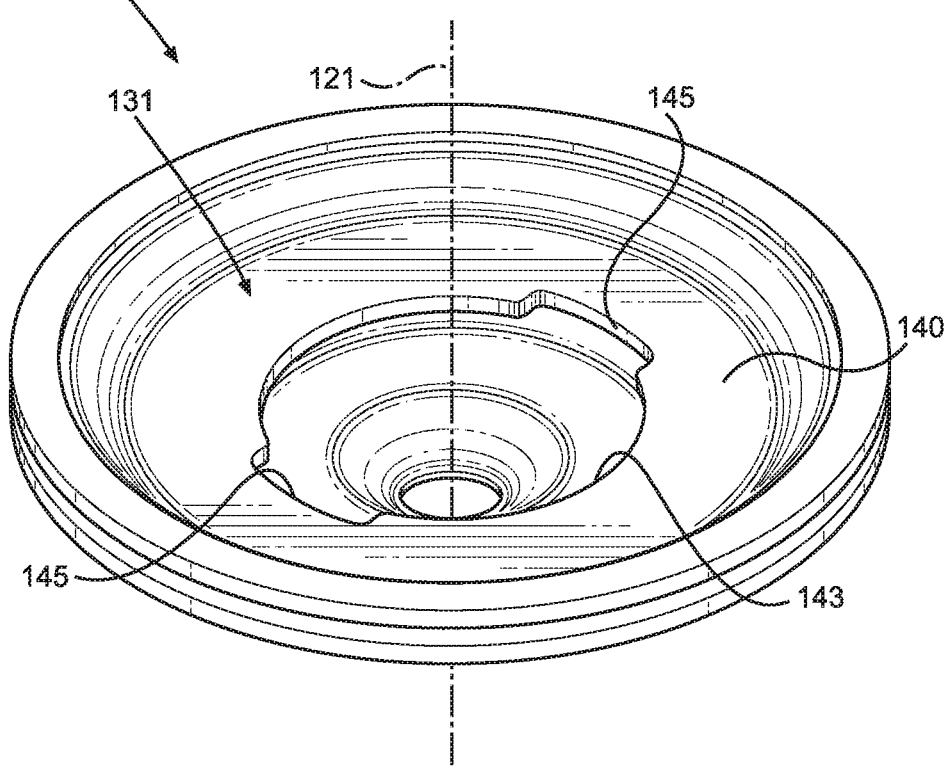
FIG. 7 is a sectional side view of the part shown in FIG. 6.
Figure 8:
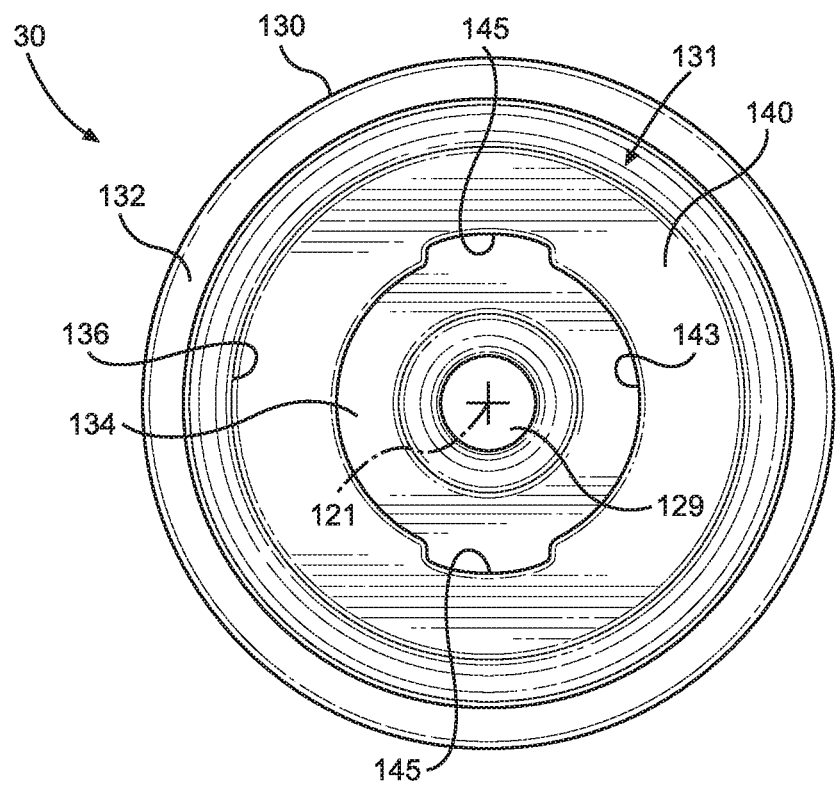
FIG. 8 is a top view of the part shown in FIG. 6.

As shown separately in FIGS. 6, 7, and 8, the reservoir device 30 has a circular cross-sectional shape centered on an axis 121. A sleeve portion 124 of the reservoir device 30 defines an axial bore 127 with an opening 129. A base portion 130 of the reservoir device 30 defines a reservoir 131 above the opening 129. The base portion 130 has a circular upper rim 132, a planar bottom wall 134, and an annular side wall 136. The side wall 136 defines the depth of the reservoir 131 axially from the rim 132 to the bottom wall 134.

The base portion 130 of the reservoir device 30 further has an intermediate wall 140 projecting radially inward from the side wall 136. The intermediate wall 140 has a circular central opening 143 and a pair of radial notches 145.

Figure 9:
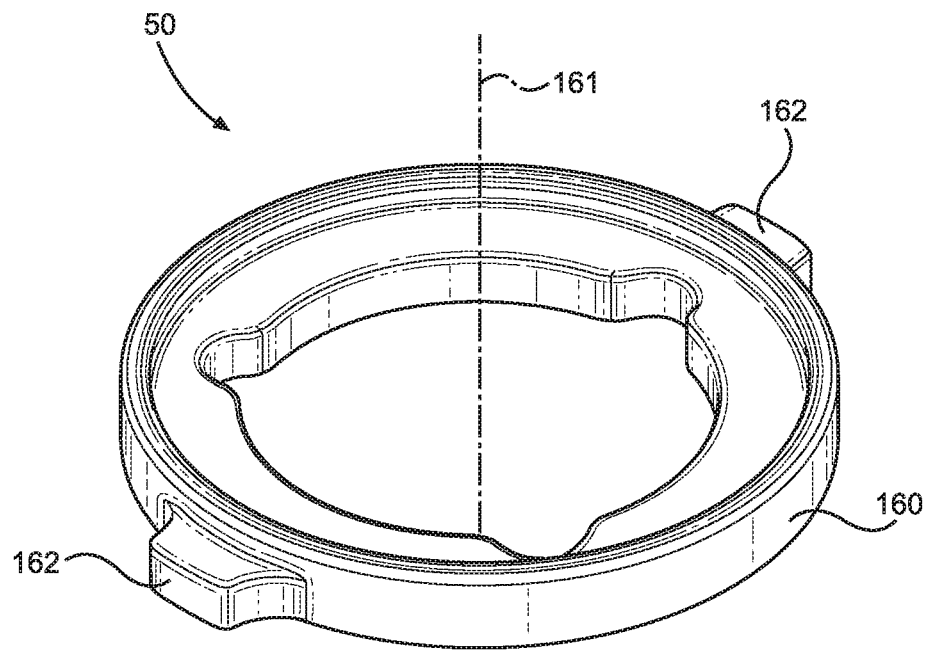
FIG. 9 is a perspective view of another part of the apparatus of FIG. 1.
Figure 10:
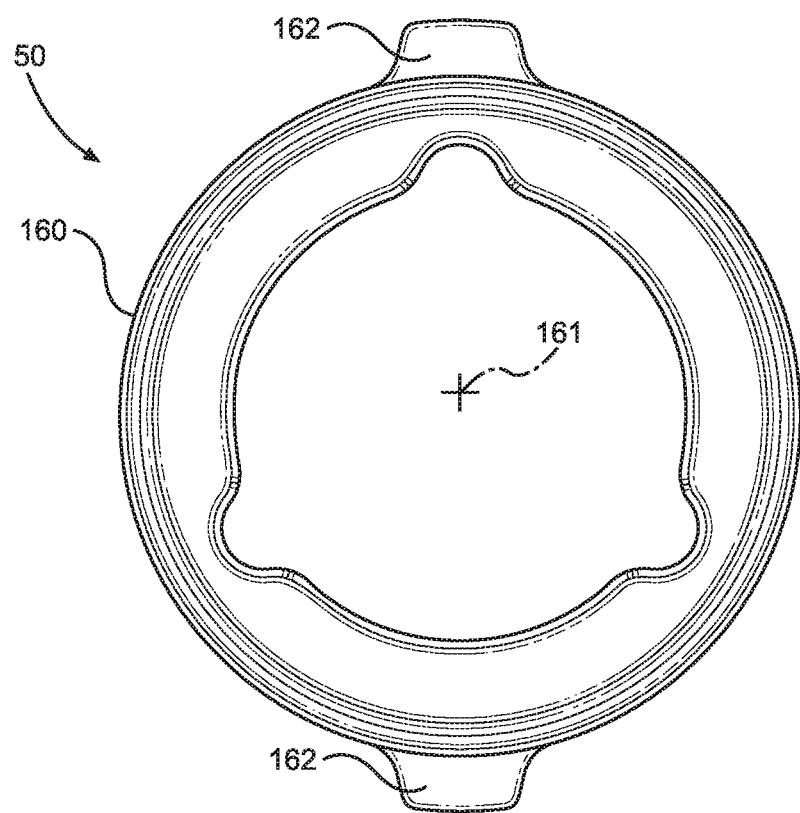
FIG. 10 is a top view of the part shown in FIG. 9.
Figure 11:
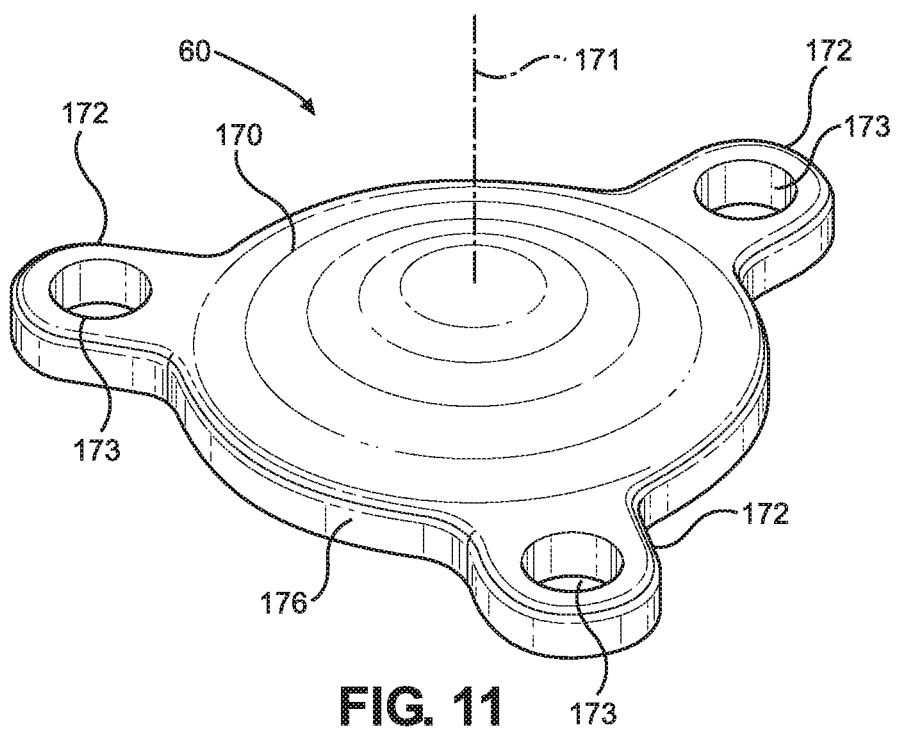
FIG. 11 is a perspective view of another part of the apparatus of FIG. 1.
Figure 12:
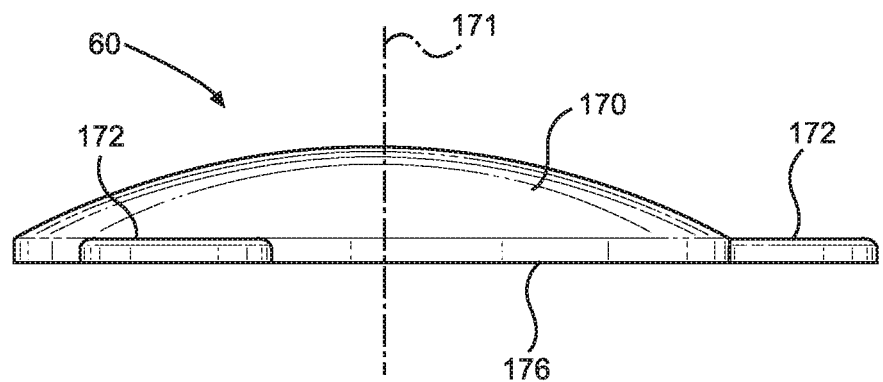
FIG. 12 is a side view of the part shown in FIG. 11.

The lock ring 50 (FIGS. 9 and 10) has a peripheral surface 160 centered on an axis 161. The peripheral surface 160 is sized to fit closely within the central opening 143 in the reservoir device 30. A pair of tabs 162 project radially outward for insertion through the notches 145 at the central opening 143. This enables the lock ring 50 to be releasably interlocked with the reservoir device 30 by moving the tabs 162 axially through the notches 145, and then rotating the lock ring 50 to move the tabs 162 beneath the intermediate wall 140 of the reservoir device 30.

Figure 13:
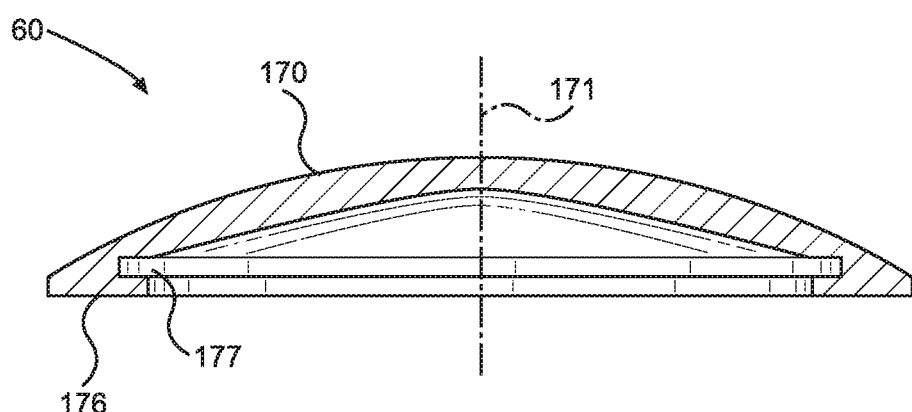
FIG. 13 is a sectional side view of the part shown in FIG. 11.
Figure 14:
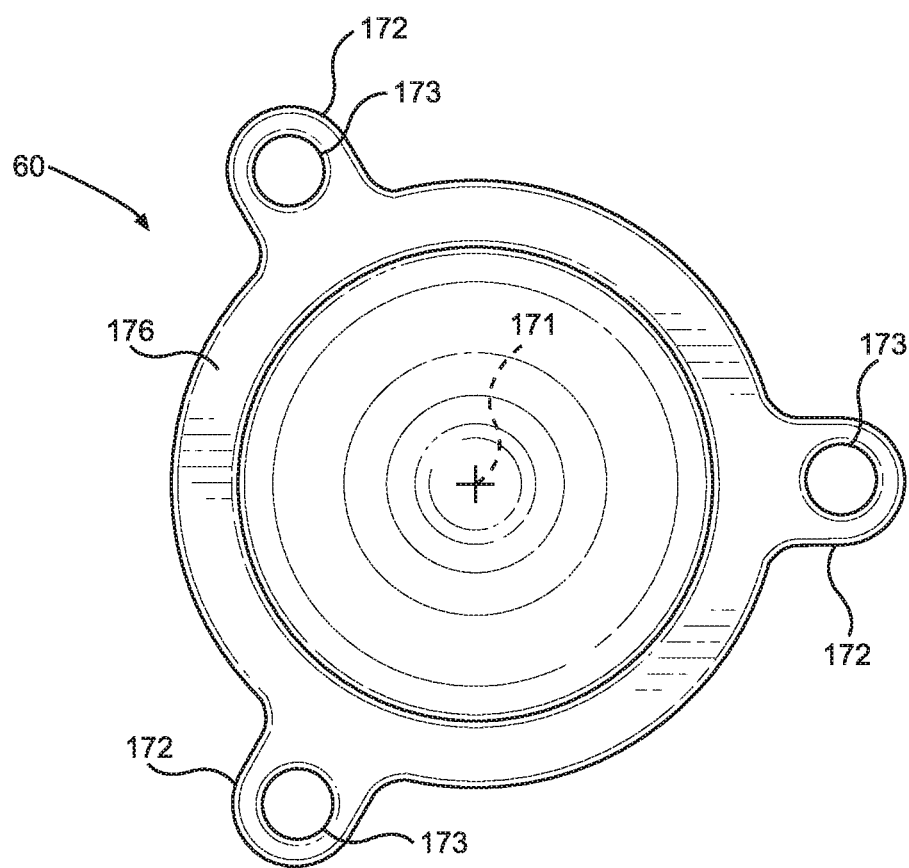
FIG. 14 is a bottom view of the part shown in FIG. 11.

As shown separately in FIGS. 11-14, the cover 60 has a circular central portion 170 centered on an axis 171. The central portion 170 is dome-shaped, as best shown in FIG. 13. Tabs 172 project radially outward from the central portion 170. Each tab 172 has an aperture 173 to receive a bone screw for fastening the cover 60 to the skull.

The central portion 170 of the cover 60 further has a lower rim 176. An internal groove 177 (FIG. 13) reaches fully around the inner periphery of the lower rim 176. The groove 177 is sized to receive the upper rim on the reservoir device 30. The cover 60 is formed of a flexible material, such as silicone, so that the rim 176 on the cover 60 can be deflected as needed for engagement with the rim 132 on the reservoir device 30.

Figure 16:
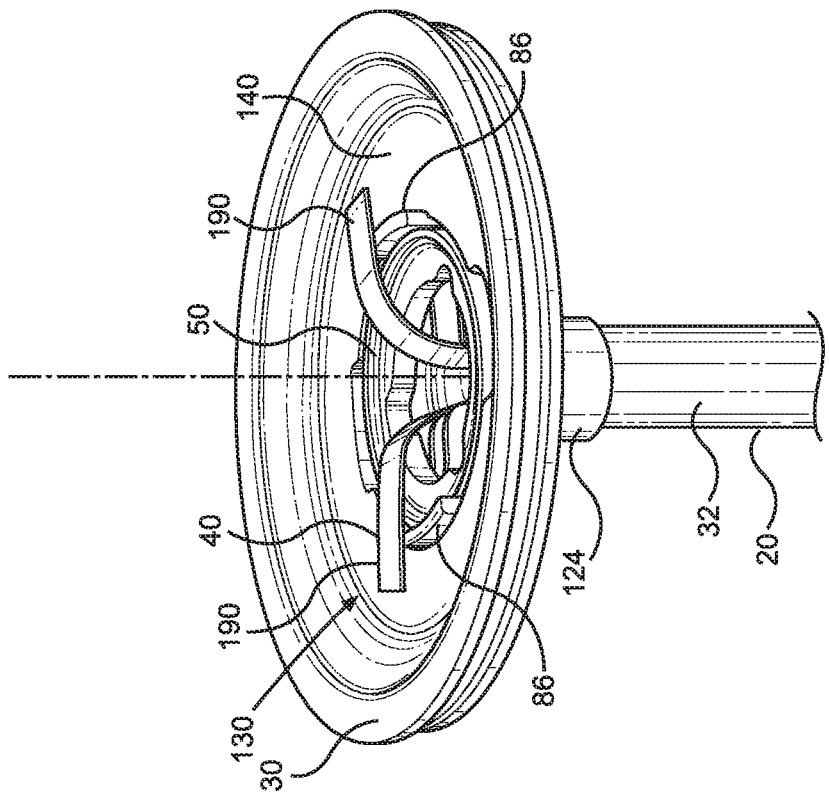
FIG. 16 is a perspective view showing the parts of FIG. 16 in a more fully assembled condition.
Figure 15:
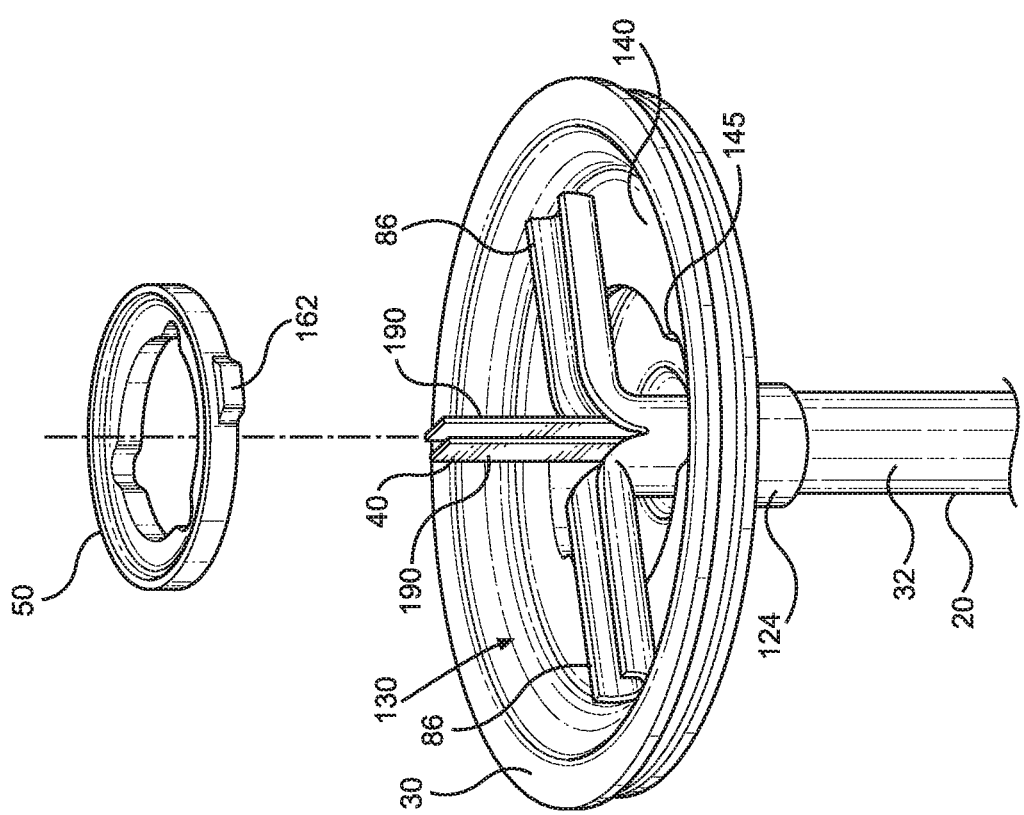
FIG. 15 is a perspective view showing the apparatus in a partially assembled condition.

The parts of the apparatus 10, including the catheter 20, reservoir device 30, nanofiber film 40, lock ring 50, and cover 60, are interconnected in the assembled apparatus 10 as shown in greater detail in FIGS. 15 and 16. The sleeve portion 124 of the reservoir device 30 is received coaxially over the proximal end portion 32 of the catheter 20. The proximal sections 86 of the side wall 72 reach into the reservoir 131 through the opening 129, and are folded to diverge radially outward in the reservoir 131. The lock ring 50 is installed over the folded sections 86 of the side wall 72, as shown in FIG. 16, to securely interlock the reservoir device 30 with the catheter 20. Opposite end portions 190 of the nanofiber film 40 also reach from the catheter 20 into the reservoir 131, and also are folded to diverge radially outward in the reservoir 131. The cover 60 provides a fluid-tight seal over the open top of the reservoir 131. In the assembled apparatus 10, the lumen 77 of the catheter 20 is patent (i.e., open and unobstructed) between its distal end portion 22 and its proximal end portion 32, with only the nanofiber film 40 disposed therein.

Figure 17:
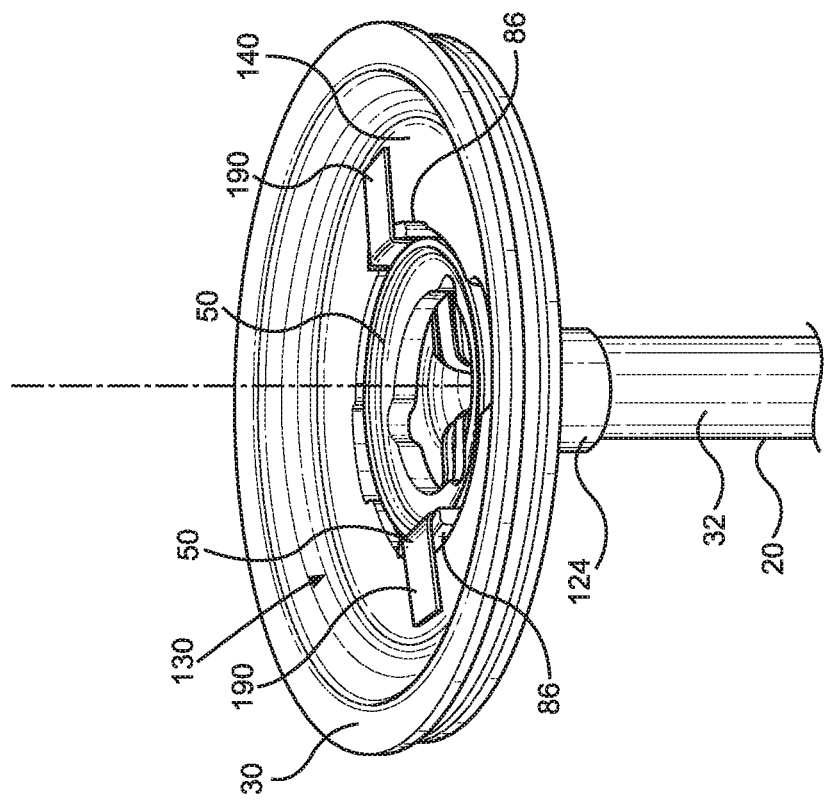
FIG. 17 is a perspective view similar to FIG. 16 an alternative arrangement of parts.

An alternative embodiment is shown in FIG. 17. In this embodiment, the lock ring 50 is installed over the folded end portions 190 of the nanofiber film 40 as well as the folded sections of the side wall 72. This retains the end portions 190 of the nanofiber film 40 securely within the reservoir 131.

Figure 18:
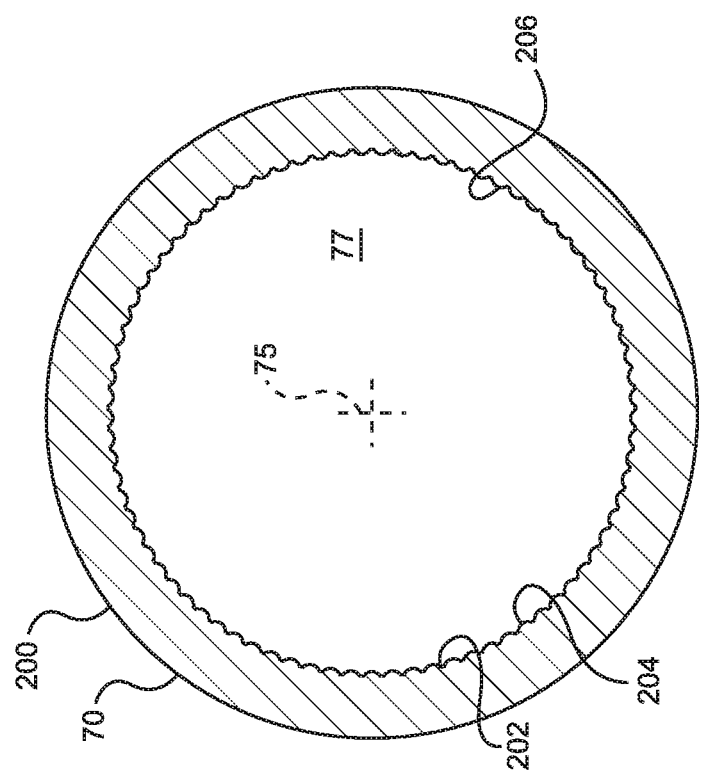
FIG. 18 is a cross-sectional view of a part of an alternative embodiment of the apparatus.

Another alternative embodiment includes an alternative catheter 200, as shown partially in FIG. 18. This catheter 200 has parts that are substantially the same as corresponding parts of the catheter 20 described above. Such parts are indicated by the use of the same references numbers in FIGS. 4, 5, and 18. The catheter 200 thus includes a tube 70 with a lumen 77 and a major length portion 88 centered on a longitudinal axis 75, as well as proximal and distal end portions with inlet openings and an outlet opening like the openings 25 and 81. Additionally, the lumen 77 has an inner surface 202 with a topographic feature 204 configured to guide migration of cancer cells through the lumen 77 from the inlet openings to the outlet opening in a direction lengthwise of the tube 70.

The topographic feature 204 in this example is a circumferential array of grooves and/or ribs or ridges 206 that are aligned lengthwise of the tube 70. Like the nanofibers described above, the grooves 206 preferably have a longitudinal orientation within about 20 degrees of the longitudinal axis 75 fully along the length of the tube 70 between the inlet openings and the outlet opening, and each groove preferably has a width of about 650+/−300 nm. In this configuration, the catheter 200 can be used as a substitute for the catheter 20 in the apparatus 10, with the proximal end portion of the tube 70 reaching into the reservoir as described above. The topographic feature 204 can then serve as a substitute for the nanofiber structure 40 by directing cancer cells to migrate through the tube 70 from a tumor to the reservoir 131.

Figure 19:
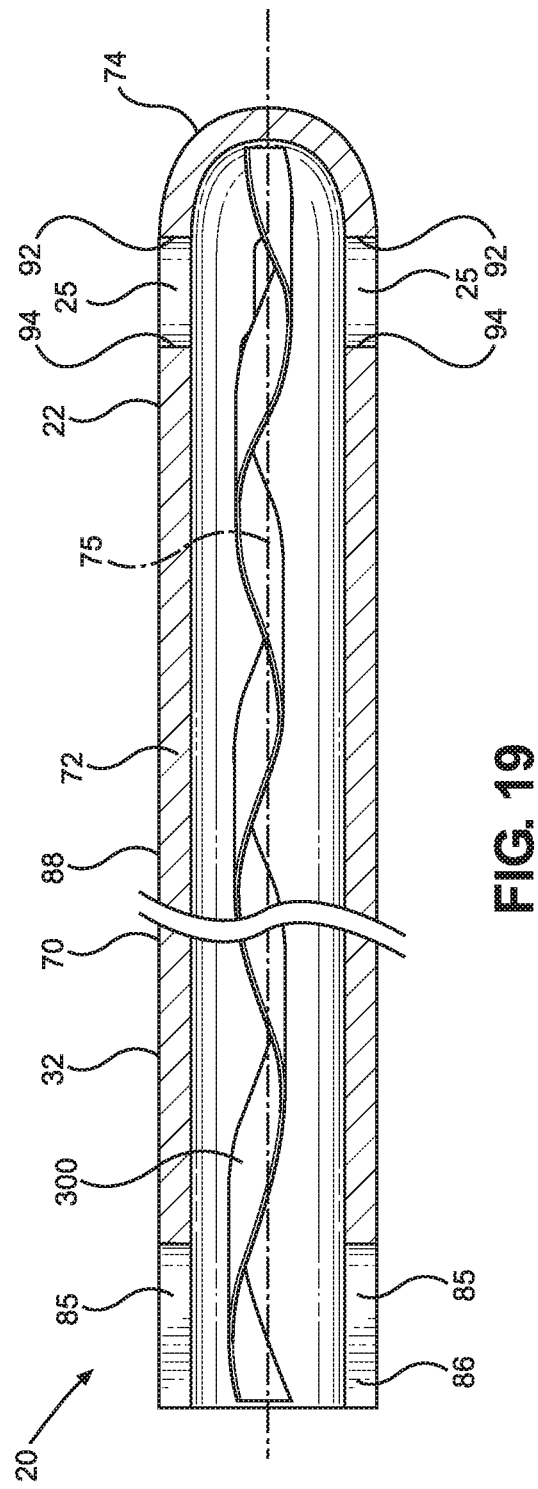
FIGS. 19-23 also cross-sectional views of additional alternative embodiments of the apparatus.
Figure 20:
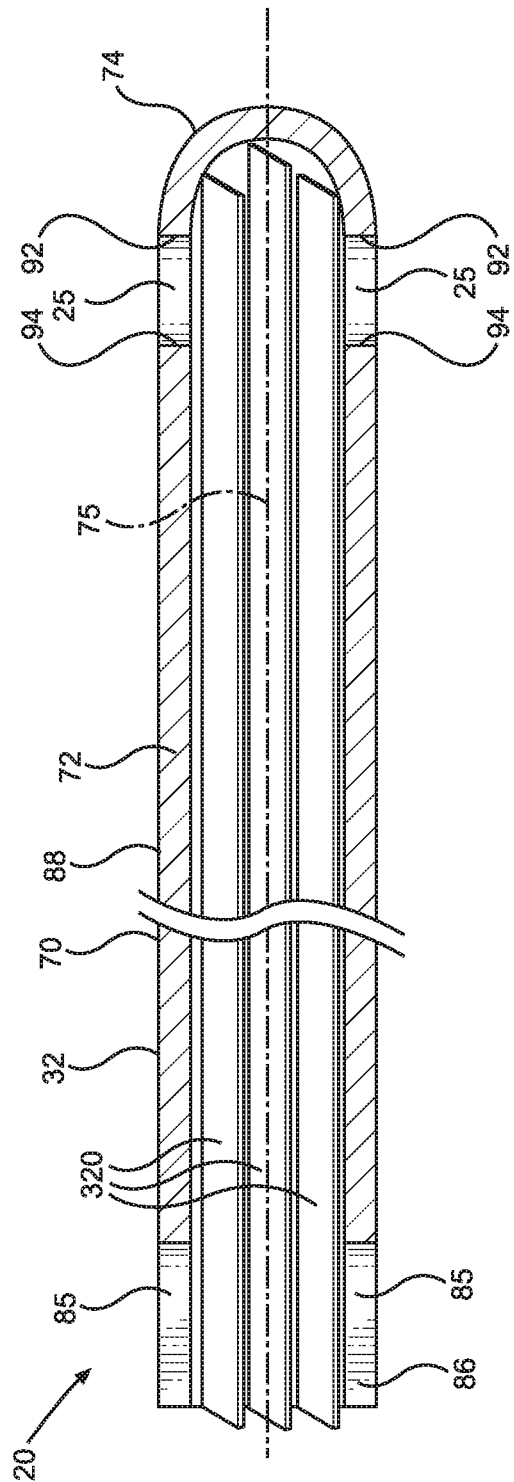
Figure 21:
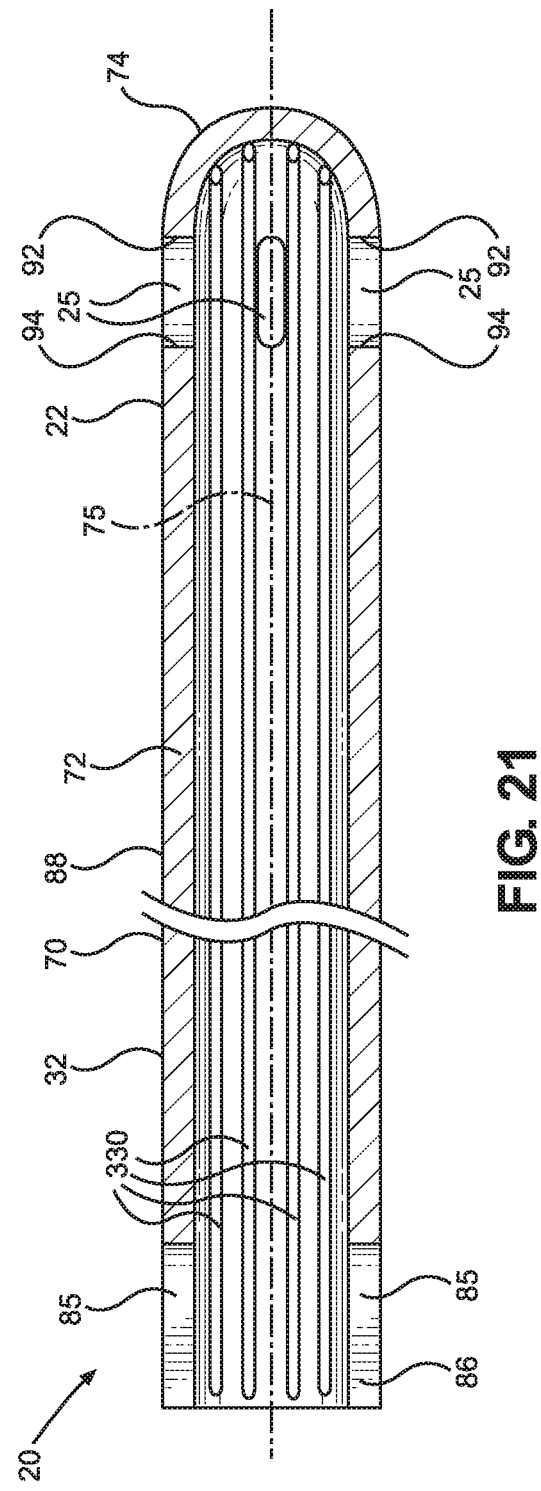
Figure 22:
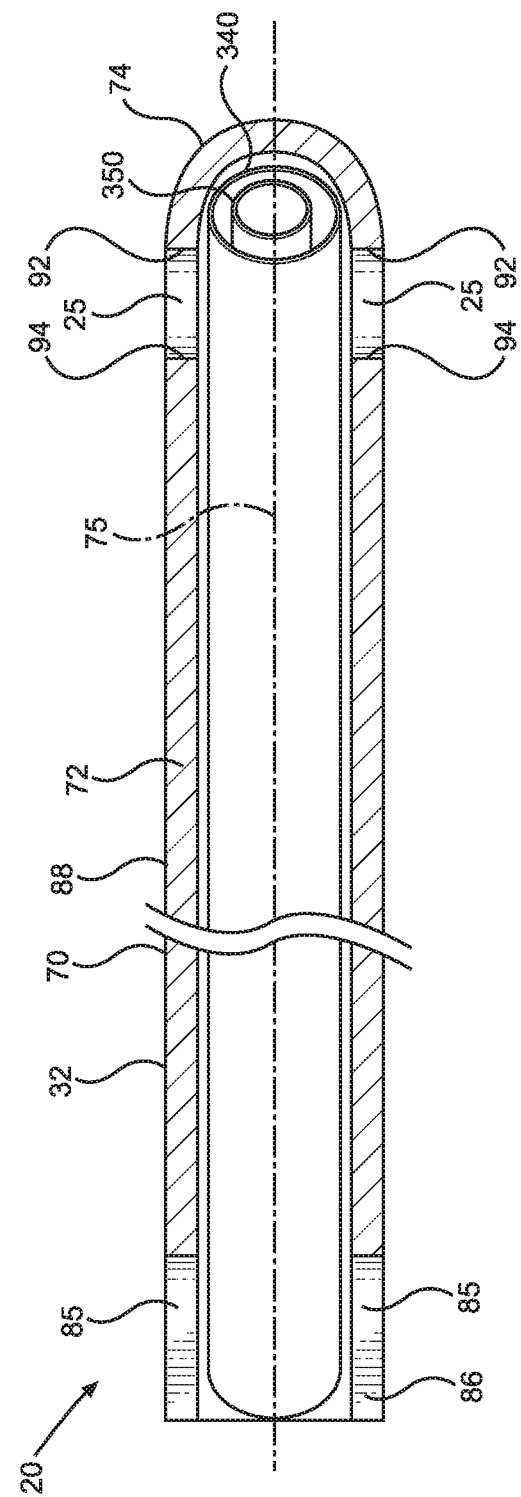
Figure 23:
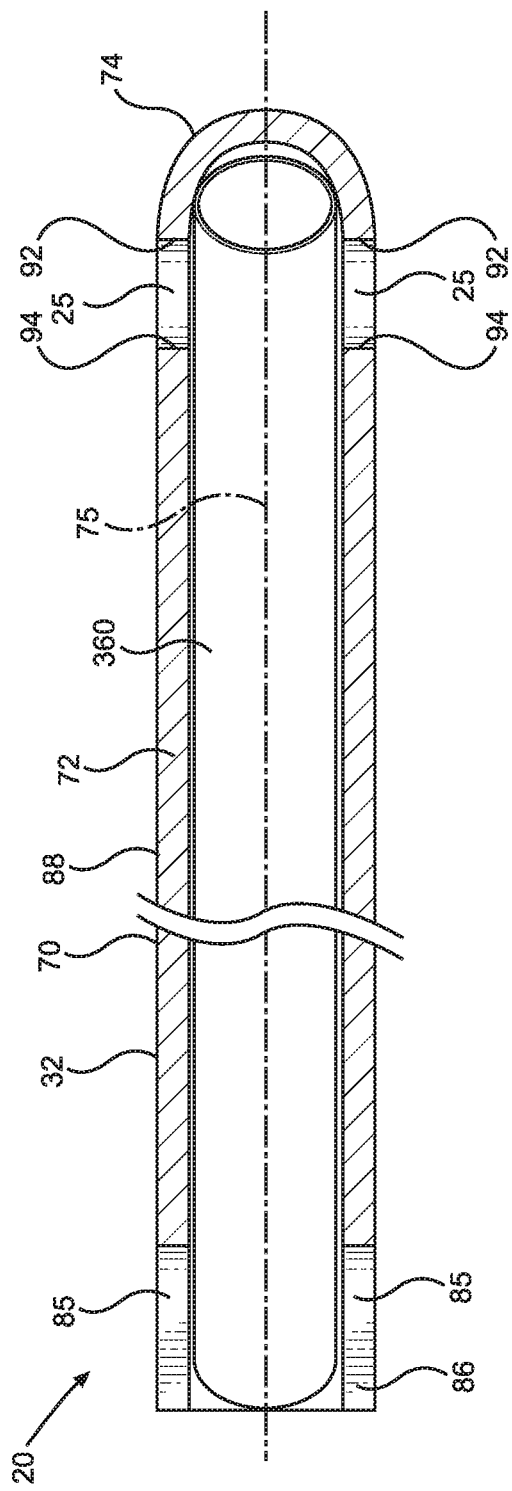

The nanofiber structure also may differ in alternative embodiments. For example, the embodiment of FIG. 19 includes a strip of nanofiber film 300 twisted into a spiral or helical configuration. The embodiment of FIG. 20 includes multiple film strips 320 in flat configurations. In the embodiment of FIG. 21, multiple film strips 330 are string-shaped. In the embodiment of FIG. 22, an inner tubular film 350 reaches concentrically through the tube 70, and is attached to the end wall 74. An outer tubular film 340 surrounds the inner tubular film 350, and is attached to the side wall 72 to reach through the tube 70 in an off-center position. In the embodiment of FIG. 23, a tubular nanofiber film 360 covers the inside of the side wall 72. The tubular film 360 may alternatively be located only proximally of the inlet openings 25 to avoid covering the inlet openings 25.

As noted previously, several embodiments are described above in the context of guiding the migration of cancer cells in a direction away from a tumor. However, the apparatus can provide bi-directional access to a tumor for excavating or transplanting cells, sampling and/or delivering small molecules, chemicals, drugs, adjuvants, cells, mRNA, proteins, or other biologics and non-biologics. The apparatus can thus provide bi-directional access to tumors or other biological material of interest. Such an apparatus can be used alone or in conjunction with other treatments of tumors including immune-therapy, chemotherapy, and/or radiation therapy.

For example, in some embodiments, the apparatus can be used to deliver one or more therapeutic agents to a treatment site. The therapeutic agent(s) (e.g., endogenous or exogenous agents, small molecules, chemicals, drugs, adjuvants, cells, mRNA, proteins, or other biologics or non-biologics) can be disposed in the reservoir or otherwise placed in contact with proximal end portions 190 of the nanofiber film 40 or other suitable nanofiber or other cell-guiding structure. The catheter 20 can be disposed with the distal end portion 22 at or adjacent to the treatment site. Once in position, the therapeutic agent(s) can be guided along the nanofiber film 40 from the reservoir, through the lumen 77, and out the inlet openings 25 to the surrounding treatment site. In some embodiments, the same apparatus can enable bi-directional access, allowing for tumor cells to be extracted from a treatment site as well as enabling delivery of therapeutic agent(s) to the treatment site.

The apparatus can also be used for repeated sampling of biological material at the treatment site, for example periodic sampling of tumor cells from within a patient's brain or other tumor site. In operation, the apparatus 20 can be positioned with the distal end portion 22 at or adjacent to the tumor site or other treatment site. The reservoir device 30 can be disposed in a position accessible to a physician, such as being coupled to a cranial aperture formed in the patient's skull. The cover 60 can be removably disposed over the reservoir device 30 to retain the extracted cells therein until removed by a clinician. Cells from the treatment site can migrate through the inlet openings 25, along the nanofiber structure 40, and into the reservoir device 30 as described above. By collecting such extracted cells at different points in time, the cells can be analyzed to evaluate progression of the tumor or to monitor other biological changes over time. This can be particularly useful in identifying clinically significant changes that may be too small to detect using imaging or other detection modalities.

ADDITIONAL SUMMARY STATEMENTS

The following summary statements are presented as examples of how features of the apparatus are suitable for use together.

An apparatus may comprise: a reservoir device defining a reservoir; a tube having a lumen; a nanofiber structure reaching outward from the lumen and into the reservoir; and a lock device interlocking the nanofiber structure with the reservoir device.

The nanofiber structure may be elongated and have a pair of opposite end portions diverging transversely within the reservoir.

The tube may have a pair of inlet openings that are spaced apart around the tube, with the nanofiber structure having a U-shape including a base and first and second legs, wherein the first leg reaches within the lumen from the base past the first inlet opening, and the second leg reaches within the lumen from the base past the second inlet opening.

The legs of the nanofiber structure may reach past the inlet openings at locations spaced transversely from the inlet openings.

The tube may have proximal and distal ends, and the legs of the nanofiber structure may be attached to the tube at attachment locations spaced distally from the inlet openings.

The tube may have a proximal end portion reaching into the reservoir.

The proximal end portion of the tube may have longitudinal sections diverging transversely within the reservoir.

An apparatus may comprise: a tube having a lumen; a reservoir device defining a reservoir; and a nanofiber structure reaching outward from the lumen and into the reservoir; wherein the tube has a proximal end portion reaching into the reservoir, and the proximal end portion of the tube has longitudinal sections diverging transversely within the reservoir.

The apparatus may further comprise a lock device engaged with the reservoir device and retaining the longitudinal sections of the tube in positions diverging within the reservoir.

The reservoir device may have an arcuate wall, and the lock device may comprise a ring with locking tabs configured to slide beneath the arcuate wall upon rotation of the ring relative to the reservoir device.

The nanofiber structure may be elongated and have a pair of opposite end portions diverging within the reservoir.

An apparatus may comprise: a reservoir device defining a reservoir having an open top; a cover configured for removable installation over the open top of the reservoir; a tube having a lumen, and further having a proximal end portion reaching into the reservoir, wherein the proximal end portion of the tube has longitudinal sections diverging transversely within the reservoir; a lock device retaining the longitudinal sections of the tube in positions diverging within the reservoir; and an elongated nanofiber structure reaching outward from the lumen and into the reservoir, the nanofiber structure having a pair of opposite terminal end portions diverging transversely within the reservoir.

The tube may have a pair of inlet openings that are spaced apart around the tube, and the nanofiber structure may have a U-shape including a base and first and second legs, wherein the first leg reaches within the lumen from the base past the first inlet opening, and the second leg reaches within the lumen from the base past the second inlet opening.

The legs of the nanofiber structure may reach past the inlet openings at locations spaced transversely from the inlet openings.

The tube may have proximal and distal ends, and the legs of the nanofiber structure may be attached to the tube at attachment locations spaced distally from the inlet openings.

The tube may have a distal end wall defining a closed distal end of the lumen, and the legs of the nanofiber structure may be attached to the tube at the distal end wall.

An apparatus may comprise: a catheter including a tube, wherein the tube has a lumen, a distal end portion with an inlet opening to the lumen, a proximal end portion with an outlet opening from the lumen, and a major length portion that is free of an opening between the distal and proximal end portions; wherein the tube has an inner surface with a topographic feature configured to guide migration of cancer cells through the lumen from the inlet opening to the outlet opening in a direction lengthwise of the tube.

The apparatus may further comprise a reservoir device defining a reservoir, wherein the proximal end portion of the tube reaches into the reservoir.

The topographic feature may comprise grooves, ribs, or ridges in the inner surface of the tube.

The tube may have a longitudinal axis, and the grooves, ribs or ridges may have a longitudinal orientation within about 20 degrees of the longitudinal axis fully and continuously along the major length portion of the tube.

The tube may have a closed distal end wall.

The tube may have a side wall, and the inlet opening may reach through the side wall.

The apparatus may further comprise a lock device interlocking the tube with the reservoir device.

An apparatus for guiding migration of cancer cells away from a treatment site may comprise: a reservoir configured to retain a cytotoxic agent therein; a catheter having a lumen in fluid communication with the reservoir, the catheter comprising a distal end portion with an inlet opening spaced apart from the reservoir, the distal end portion configured to be disposed at the treatment site; and a nanofiber structure disposed within the catheter lumen and extending from the distal end portion into the reservoir, the nanofiber structure configured to guide migration of cancer cells from the inlet opening into the reservoir.

An apparatus for delivering a therapeutic agent to a treatment site may comprise: a reservoir configured to retain a therapeutic agent therein; a catheter having a lumen in fluid communication with the reservoir, the catheter comprising a proximal end portion adjacent to the reservoir and a distal end portion with an inlet opening, the distal end portion configured to be disposed at the treatment site; and a nanofiber structure disposed within the catheter lumen and extending from the distal end portion into the reservoir, the nanofiber structure configured to guide the therapeutic agent from the reservoir, through the inlet opening, and to the treatment site.

The therapeutic agent may comprise exogenous cells.

The therapeutic agent may comprise endogenous cells.

A method for guiding migration of cells away from a treatment site may comprise: disposing a distal end portion of a catheter adjacent to the treatment site, the distal end portion comprising an inlet opening in communication with a catheter lumen, the catheter having a proximal portion coupled to a reservoir, wherein a nanofiber structure is disposed within the catheter lumen, the nanofiber structure extending from the distal end portion to the reservoir; and receiving, in the reservoir, cells that have migrated from the treatment site along the nanofiber structure.

The cells may comprise cancer cells, the treatment site may comprise a tumor site, and the reservoir may contain a cytotoxic agent.

The cells may comprise glioma cells, the treatment site may comprise a brain tumor site, and the reservoir may contain a cytotoxic agent.

The method may further comprise forming a cranial aperture in a patient's skull, wherein disposing the distal end portion of the catheter adjacent to the treatment site comprises inserting the catheter through the cranial aperture and disposing the reservoir within or adjacent to the cranial aperture.

The method may further comprise disposing a cover over the reservoir and fastening the cover to the patient's skull.

A method of sampling cancer cells from a treatment site may comprise: disposing a distal end portion of a catheter adjacent to the treatment site, the distal end portion comprising an inlet opening in communication with a catheter lumen, the catheter having a proximal portion coupled to a reservoir, wherein a nanofiber structure is disposed within the catheter lumen, the nanofiber structure extending from the distal end portion to the reservoir; after a first period of time, retrieving a first plurality of cells that have migrated from the treatment site, along the nanofiber structure, and into the reservoir; and after a second period of time longer than the first, retrieving a second plurality of cells that have migrated from the treatment site, along the nanofiber structure, and into the reservoir.

The method may further comprise comparing the first plurality of cells and the second plurality of cells to evaluate progression of a tumor at the treatment site.

The second period of time may be at least 1 week longer than the first period of time.

The second period of time may be at least 1 month longer than the first period of time.

The method may be a method in which the catheter is not removed between the first period of time and the second period of time.

The cells may comprise glioma cells and the treatment site may comprise a brain tumor site.

The method further comprise forming a cranial aperture in a patient's skull, wherein disposing the distal end portion of the catheter adjacent to the treatment site comprises inserting the catheter through the cranial aperture and disposing the reservoir within or adjacent to the cranial aperture.

The method may further comprise disposing a cover over the reservoir, and fastening the cover to the patient's skull.

A method for bi-directionally accessing a treatment site may comprise: disposing a distal end portion of a catheter adjacent to the treatment site, the distal end portion comprising an inlet opening in communication with a catheter lumen, the catheter having a proximal portion coupled to a reservoir, wherein a nanofiber structure is disposed within the catheter lumen, the nanofiber structure extending from the distal end portion to the reservoir; after a first period of time, retrieving a first plurality of cells that have migrated from the treatment site, along the nanofiber structure, and into the reservoir; after a second period of time, disposing a therapeutic agent in the reservoir such that the therapeutic agent migrates along the nanofiber structure from the reservoir, out the inlet opening, and to the treatment site.

The cells may comprise cancer cells and the treatment site may comprise a tumor site.

The cells may comprise glioma cells and the treatment site may comprise a brain tumor site.

The method may further comprise forming a cranial aperture in a patient's skull, wherein disposing the distal end portion of the catheter adjacent to the treatment site comprises inserting the catheter through the cranial aperture and disposing the reservoir within or adjacent to the cranial aperture.

The method may further comprise disposing a cover over the reservoir, and fastening the cover to the skull.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims. The use herein of the terms "including," comprising," and "having" and variations thereof, is meant to encompass the elements listed thereafter and equivalents thereof as well as additional elements. As used herein, "and/or" refers to and encompasses any and all possible combinations of the associated listed items, as well as the lack of combinations where interpreted in the alternative ("or").

What is claimed is:

1. An apparatus for guiding cells, the apparatus comprising:
- an axially elongated tube having a sidewall defining a lumen within the tube, the lumen having a closed distal end and an open proximal end;
- an inlet formed in the sidewall, the inlet opening being elongated along the axial direction;
- a reservoir device defining a reservoir within the reservoir device, wherein the reservoir comprises a base portion having a reservoir base opening, and wherein a proximal end portion of the tube extends through the reservoir base opening such that the tube lumen is in fluid communication with the reservoir;
- a lock ring for securing the proximal end portion of the tube to the base portion of the reservoir by pinching the sidewall of the tube between the lock ring and the base portion of the reservoir; and
- a nanofiber structure having a distal end portion disposed within the lumen at a position distal to the inlet opening, the nanofiber structure extending in the axial direction outward from the lumen and into the reservoir device to a location within the reservoir,
- wherein the tube lumen is patent between its distal end and proximal end with only the nanofiber structure disposed therein.

2. An apparatus as defined in claim 1, wherein the nanofiber structure is configured as a strip of nanofiber film.

3. An apparatus as defined in claim 1, wherein the tube further has a major length portion reaching from the inlet opening to the proximal end, wherein the major length portion of the tube is free of openings.

4. An apparatus as defined in claim 3, wherein the nanofiber structure is unattached to the major length portion of the tube.

5. An apparatus as defined in claim 1, wherein the inlet opening has parallel opposite side edges reaching between rounded opposite end edges.

6. An apparatus as defined in claim 1, wherein the reservoir device is mounted on a proximal end portion of the tube.

7. An apparatus as defined in claim 6, wherein the reservoir device has a sleeve portion received over the tube at a proximal end of the tube, and the nanofiber structure reaches through the sleeve portion of the reservoir device.

8. An apparatus as defined in claim 7, wherein the reservoir device has an open top, and further comprising a cover configured for removable installation over the open top of the reservoir device.

9. An apparatus as defined in claim 1, wherein the nanofiber structure is interlocked with the reservoir device.

10. The apparatus of claim 1, wherein the lock ring has a central opening and is configured such that, when the lock ring secures the proximal end portion of the tube to the base portion of the reservoir, the central opening of the lock ring is aligned with the reservoir base opening and with the lumen.

11. An apparatus for guiding migration of cancer cells away from a tumor, the apparatus comprising:
- a reservoir device defining a reservoir therein, the reservoir comprising a base portion having a reservoir base opening;
- a catheter comprising an elongated tubular sidewall defining a lumen, the catheter extending between (a) an outlet opening at a proximal end portion of the catheter that extends through the reservoir base opening and into the reservoir and (b) a distal end portion of the catheter, wherein the lumen is in fluid communication with the reservoir via the outlet opening, and wherein distal end portion of the sidewall includes an inlet opening, the inlet opening being elongated along an axial length of the catheter and defining a trailing edge and a leading edge;
- a lock ring for securing the proximal end portion of the catheter to the base portion of the reservoir by pinching the sidewall of the catheter between the lock ring and the base portion of the reservoir; and
- a nanofiber structure disposed within the lumen of the catheter, the nanofiber structure having a distal end region distal to the leading edge of the inlet opening at the distal end portion of the catheter and a proximal end region at a location within the reservoir,
- wherein the distal end portion of the catheter is configured to penetrate a tumor of a living patient, and
- wherein, when the distal end portion of the catheter is positioned in the tumor, tumor cells move through the inlet openings and into contact with the nanofiber structure, and wherein the nanofiber structure is configured to guide migration of the cancer cells to the proximal end portion of the catheter and into the reservoir.

12. The apparatus of claim 11, wherein the catheter has a rounded distal tip and is configured to extend within a brain of the patient with the distal end portion penetrating a brain tumor, and wherein the reservoir device is configured to be implanted within a cranial aperture.

13. The apparatus of claim 11, wherein the catheter has a distal end wall defining a closed distal end of the lumen.

14. The apparatus of claim 11, wherein the proximal end region of the nanofiber structure extends through the outlet opening in a proximal direction, then extends radially outwardly from a longitudinal axis of the catheter and into the reservoir.

15. The apparatus of claim 11, wherein the inlet opening is an axially elongated slot.

16. The apparatus of claim 11, wherein the inlet opening is one of multiple inlet openings that are spaced apart around the sidewall at the distal end portion of the catheter.

17. An apparatus for guiding migration of cancer cells away from a tumor in a living patient, the apparatus comprising:
- a reservoir device defining a reservoir therein, the reservoir comprising a base portion having a reservoir base opening;
- a catheter comprising an elongated tubular sidewall defining a lumen, the catheter extending between (a) an outlet opening at a proximal end portion of the catheter that extends through the reservoir base opening and into the reservoir and (b) a distal end portion of the catheter, wherein a distal end portion of the sidewall includes an inlet opening, the distal end portion configured to penetrate the tumor, thereby placing the inlet opening in fluid communication with the lumen and the reservoir;
- a lock ring for securing the proximal end portion of the catheter to the base portion of the reservoir by pinching the sidewall of the tube between the lock ring and the base portion of the reservoir; and
- a nanofiber structure disposed within the lumen of the catheter, the nanofiber structure having a distal end region adjacent the inlet opening at the distal end portion of the catheter and a proximal end region at a location within and interlocked with the reservoir, wherein the nanofiber structure is configured to guide migration of the cancer cells from the distal end portion of the catheter into the reservoir.

18. The apparatus of claim 17, wherein the apparatus is configured for bi-directional sampling of biological matter.

19. The apparatus of claim 17, wherein the apparatus is configured for bi-directional access to the tumor for excavating or transplanting cells and for delivering a therapeutic agent to the cells.

20. The apparatus of claim 17, wherein the catheter is configured to extend within a brain of the patient with the distal end portion penetrating a brain tumor, and wherein the reservoir device is configured to be implanted within a cranial aperture.

21. The apparatus of claim 17, wherein the catheter has a distal end wall defining a closed distal end of the lumen.

22. The apparatus of claim 17, wherein the inlet opening is axially elongated, and wherein the nanofiber structure extends axially within the lumen of the catheter such that the distal end region of the nanofiber structure is disposed adjacent to the inlet opening.

\* \* \* \* \*